(12) United States Patent
Miles et al.

(10) Patent No.: US 7,157,232 B2
(45) Date of Patent: Jan. 2, 2007

(54) METHOD TO DETECT THE END-POINT FOR PCR DNA AMPLIFICATION USING AN IONICALLY LABELED PROBE AND MEASURING IMPEDANCE CHANGE

(75) Inventors: Robin R. Miles, Danville, CA (US); Phillip Belgrader, Severna Park, MD (US); Christopher D. Fuller, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 251 days.

(21) Appl. No.: 11/020,731

(22) Filed: Dec. 21, 2004

(65) Prior Publication Data

US 2005/0136466 A1 Jun. 23, 2005

Related U.S. Application Data

(63) Continuation-in-part of application No. 09/738,461, filed on Dec. 13, 2000, now abandoned.

(51) Int. Cl.
*C12Q 1/68* (2006.01)
*C12P 19/34* (2006.01)

(52) U.S. Cl. .......................... 435/6; 435/91.2
(58) Field of Classification Search .................... 435/6, 435/91.2
See application file for complete search history.

(56) References Cited

U.S. PATENT DOCUMENTS

| | | | | |
|---|---|---|---|---|
| 5,210,015 A | * | 5/1993 | Gelfand et al. ................. | 435/6 |
| 6,764,583 B1 | * | 7/2004 | Miles ........................ | 204/452 |
| 2002/0072054 A1 | * | 6/2002 | Miles et al. ................... | 435/6 |
| 2004/0100284 A1 | * | 5/2004 | Lee et al. ................... | 324/663 |
| 2005/0095624 A1 | * | 5/2005 | Kim et al. ..................... | 435/6 |
| 2005/0130183 A1 | * | 6/2005 | Oh et al. ....................... | 435/6 |

OTHER PUBLICATIONS

Holland et al., PNAS USA 88, 7276-7280 (1991).*
Ye, Y., et al., "DNA Electrochemical Behaviours, Recognition and Sensing by Combining with PCR Techniques," Sensors, 2003, 3, pp. 128-145.
Gourley, P., "Micro- and Nanofabricated Electro-optical Mechanical Systems for Biomedical and Environmental Applications," SPIE, vol. 3258, pp. 82-90, 1998.

* cited by examiner

Primary Examiner—Kenneth R. Horlick
(74) Attorney, Agent, or Firm—Eddie E. Scott

(57) ABSTRACT

Impedance measurements are used to detect the end-point for PCR DNA amplification. A pair of spaced electrodes are located on a surface of a microfluidic channel and an AC or DC voltage is applied across the electrodes to produce an electric field. An ionically labeled probe will attach to a complementary DNA segment, and a polymerase enzyme will release the ionic label. This causes the conductivity of the solution in the area of the electrode to change. This change in conductivity is measured as a change in the impedance been the two electrodes.

9 Claims, 2 Drawing Sheets

METHOD TO DETECT THE END-POINT FOR PCR DNA AMPLIFICATION USING AN IONICALLY LABELED PROBE AND MEASURING IMPEDANCE CHANGE

CROSS-REFERENCE TO RELATED APPLICATIONS

This application is a Continuation-in-part of U.S. patent application Ser. No. 09/738,461 filed Dec. 13, 2000, abandoned, titled, "A Sensor Using Impedance Change to Detect the End-point for PCR DNA Amplification", which is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of Endeavor

The present invention relates to the detection of pathogen in a microfluidic channel, particularly to detection of the end-point for PCR DNA amplification and more particularly to the use of an ionically labeled probe and impedance measurement for detecting that end-point.

2. State of Technology

In a typical PCR assay, double stranded DNA is denatured into two single stranded DNA molecules, and a fluorescent label is released when a probe of known sequence attaches to a single-stranded DNA. The fluorescent label is detected as a fluorescent signal, which is detected optically. This optical assay is commonly known as the Taqman assay.

SUMMARY OF THE INVENTION

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention substitutes an ionic probe for the fluorescence probe and replaces optical measurements with electrical impedance methods thereby reducing the cost of PCR instrumentation. The invention utilizes a pair of electrodes located in a fluidic channel with an electric field produced therebetween. The fluid around the DNA when labeled by an ionic label becomes more conductive, thus resulting in a change in impedance between the electrodes, which is measured by an impedance sensor.

An embodiment of the present invention detects pathogens in a sample fluid using impedance measurements.

Another embodiment of the invention provides a sensor, which uses impedance measurements to detect the end-point for PCR DNA amplification.

Another embodiment of the invention provides a method and apparatus to detect the presence of a specific type of pathogen in a biological sample using PCR amplification where a specific sequence attaches to a single-stranded DNA using anionic label instead of a fluorescent label, and using an electronic system instead of an optical system for detection.

Another embodiment of the invention uses electronic detection in place of optical detection in a typical PCR assay.

Another embodiment of the invention detects the endpoint for PCR DNA amplification using an ionically labeled probe for attaching to the complementary DNA segment causing release of an ionic label which results in a change in impedance between a pair of spaced electrodes located in fluidic channel through which the DNA segment passes.

Another embodiment of the invention provides an impedance sensor operatively connected to a pair of electrodes located in a fluidic channel with an AC or DC voltage imposed thereon creating and electric field through which pathogen (DNA segments) pass, and ionically labeling selected DNA segments causing a change in impedance across the electrodes, which is measured by the sensor.

Various objects and advantages of the present invention will become apparent from the following description and accompanying drawing. The invention involves the use of impedance measurements to detect the end-point for PCR DNA amplification. Compared to the prior optical (Taqman) assay approach, the invention utilized an ionic probe rather than a fluorescence probe and utilizes electronic detection instead of optical detection. This is accomplished by positioning a pair of electrodes in a fluidic channel through which a sample is directed and producing an electric field across the electrodes; and an ionically labeled probe when attached to a complementary DNA segment causes the polymerase enzyme to release an ionic label causing a change in conductivity in the sample adjacent the electrodes, which change is measured as a change of impedance between the electrodes. By the substitution of an ionic probe and electronic detection in place of the fluorescent probe and optical detection, the cost of PCR instrumentation is reduced.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and form a part of the disclosure, illustrate an embodiment of the invention and, together with the description, serve to explain the principles of the invention.

DETAILED DESCRIPTION OF THE INVENTION

Figure 1:
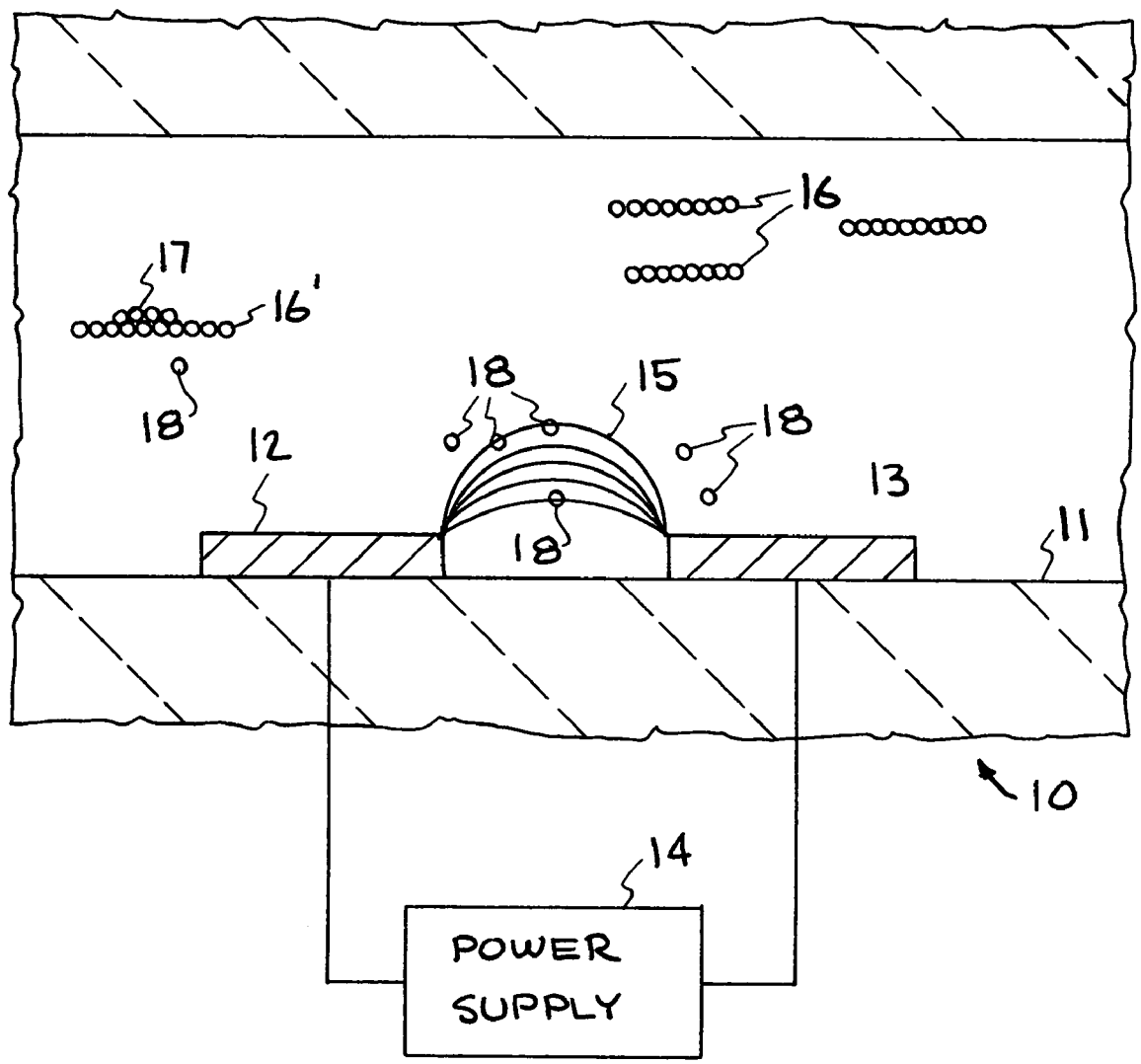
FIG. 1 is a schematic cross-sectional view of a fluidic channel illustrating the spaced electrodes and the method of detection as ionically labeled DNA segments pass across an electric field between the electrodes.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

The present invention is directed to a method and apparatus using impedance measurements to detect the end-point for PCR DNA amplification.

One principle method to detect the presence of a specific type of pathogen in a biological sample is to use PCR amplification where a specific sequence attaches to single-stranded DNA. As a polymerase enzyme completes the complementary strand, a fluorescent label is released from the probe. This label is detected as a fluorescent signal which is detected optically. The present invention replaces the fluorescent label with an ionic label. After each amplification cycle, the fluid around the DNA will become increasingly more conductive. This conductivity can be measured as a change in impedance between two electrodes. This will result in the replacement of an expensive optical system with a less expensive electronic system.

In a typical PCR assay, double stranded DNA is denatured into two single stranded DNA molecules. Using the present invention an ionically labeled probe will attach to a complementary DNA segment, as seen in FIG. 1. The polymerase enzyme will release an ionic label, which is trapped in an electric field across two electrodes as shown in FIG. 1. The conductivity of the solution flowing across the electrodes is changed by the ionic labels. This change of conductivity is measured by the sensor of FIG. 2 as a change in the impedance between the two electrodes.

Figure 2:
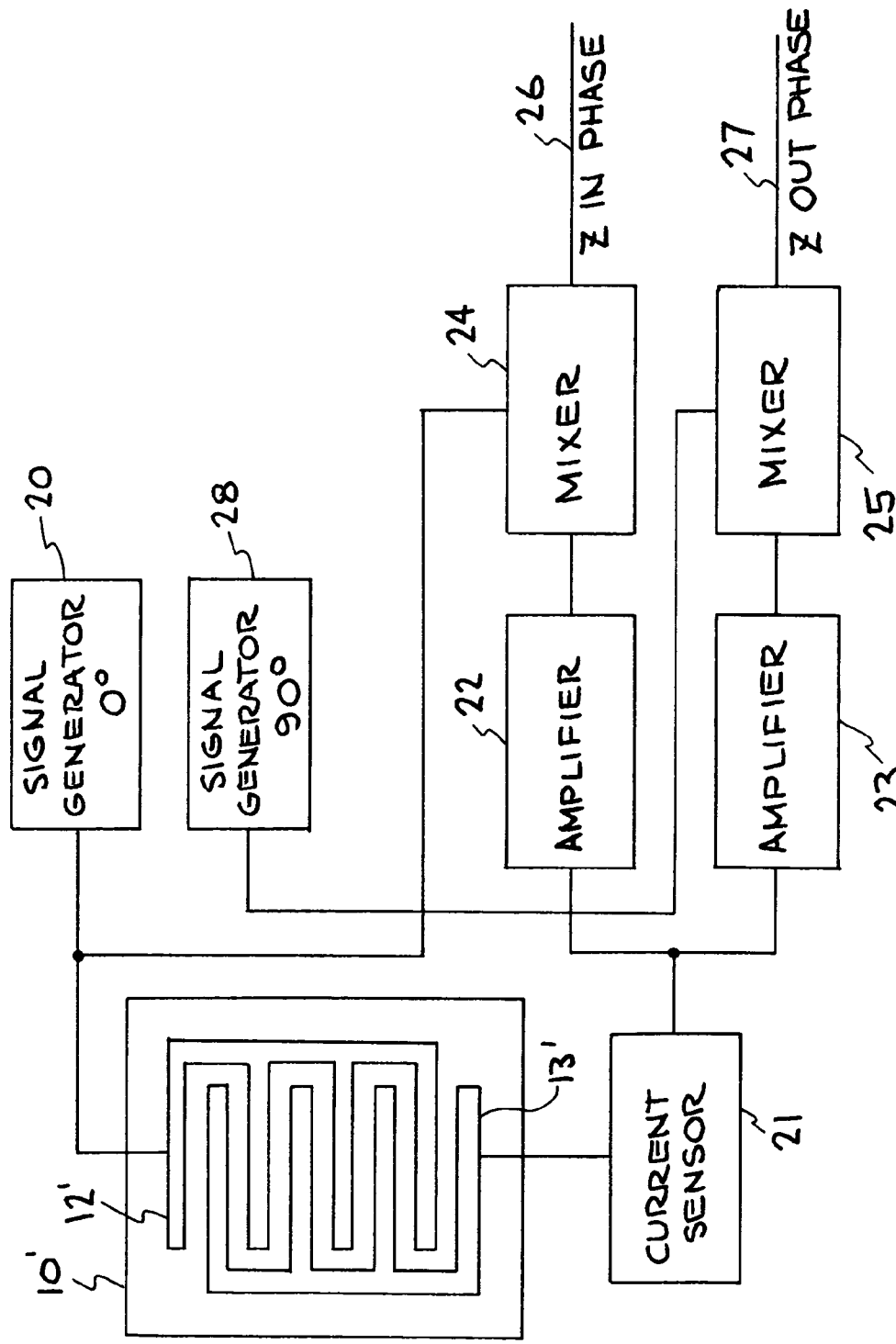
FIG. 2 schematically illustrates an embodiment of an impedance sensor adapted to be attached to the electrodes of FIG. 1.

The apparatus for carrying out the detection method of the present invention, basically involves a fluidic or microfluidic channel in which a pair of spaced electrodes are positioned and across which an alternating current (AC) voltage, produced by an AC power supply, or a direct current (DC) voltage, produced by a DC power supply, is impressed causing the formation of an electric field therebetween, which functions to trap, collect or concentrate the released labeled ions as described above. The electrodes are electrically connected to an impedance sensor, such as illustrated in FIG. 2 for measuring change in impedance between the electrodes caused by the trapping of the labeled ions in the electric field.

Referring now to the drawings, FIG. 1 illustrates a partial, enlarged cross-section of a fluidic or microfluidic device generally indicated at 10 having at least one fluidic channel 11 on the surface of which are located electrodes 12 and 13 connected to an AC power supply 14 for imposing an AC voltage across the electrodes thereby producing an electric field 15 therebetween. Electrodes 12 and 13 may be of an interdigitated type as shown in FIG. 2.

As single stranded DNA molecules 16 in a sample fluid pass through channel 11, ionically labeled probes 17 will attach to a complementary DNA segments 16', as shown, and the polymerase enzyme will release a labeled ion 18, which ions 18 are trapped in the electric field 15 causing a change in the conductivity of sample fluid intermediate electrodes 12 and 13. This change in conductivity is measured as a change in the impedance between electrodes 12 and 13 by the sensor of FIG. 2.

Examples of the ionically labeled probes 17 and methods of producing the ionically labeled probes 17 will now be described. Referring to FIG. 1, a DNA molecule 16 is shown in the sample fluid as the sample fluid passes through the channel 11. An ionically labeled probe 17 is attached to a complementary DNA segment 16'. The ionically labeled probe 17 in this example is an electroactive indicator. Electroactive indicators are know in the art, for example the article "DNA Electrochemical Behaviors, Recognition and Sensing by Combining with PCR Technique," by Yongkang Ye and Huangxian, in *Sensors* 2003, 3, 128–145 describes electroactive indicators and labels on page 131. The disclosure of the article "DNA Electrochemical Behaviors, Recognition and Sensing by Combining with PCR Technique," by Yongkang Ye and Huangxian, in *Sensors* 2003, 3, 128–145 is incorporated herein by reference. The electroactive indicator is attached to the complementary DNA segment 16'. The polymerase enzyme will release the labeled ion 18 from the electroactive indicator. The labeled ion 18 is trapped in the electric field 15 as shown in FIG. 1. The labeled ion 18 in the electric field 15 causes a change in the conductivity of the sample fluid intermediate electrodes 12 and 13. This change in conductivity is measured as a change in the impedance between electrodes 12 and 13.

In another example, the ionically labeled probes 17 are cationic metal complexes. For example, a cationic label can be at one end of the probe (say the 5' end) and an anionic label can be at the other end (say the 3' end). One label produces a change that can be measured in an electrochemical detector after the probe is cleaved by Taq polymerase during PCR. When the probe hybridizes downstream of the PCR primer being extended, the Taq polymerase will displace and cleave the probe (e.g., Taqman). The label 18 will then be released and the electrochemical properties of the cleaved molecule and or solution will be changed. A cationic metal complex or ionically labeled probe 17 will release a labeled ion 18. The ion 18 will be trapped in the electric field 15 causing a change in the conductivity of sample fluid intermediate electrodes 12 and 13. This change in conductivity is measured as a change in the impedance between electrodes 12 and 13 by the sensor of FIG. 2.

In yet other examples, electrophores can be used as labels used to enhance mass spectrometry analysis of DNA. It is to be understood that the ionically labeled probes 17 and methods of producing the ionically labeled probes are susceptible to modifications and alternative forms. The ionically labeled probes 17 are not limited to the particular forms and examples described and can be produced by various modifications, equivalents, and alternatives.

The electrodes 12 and 13 may be formed in the surface of the channel 11. The embodiment of the FIG. 2 sensor comprises electrodes 12' and 13' located in a microchannel device 10', with a 0° generator 20 electrically connected to electrode 12' and a current sensor 21 electrically connected to electrode 13'. A pair of amplifiers 22 and 23 are connected in parallel to current sensor 21, with mixers 24 and 25 operatively connected to amplifiers 22 and 23, which measure the impedance (z) in-phase, indicated at 26, and out-of-phase, indicated at 27, of the components of the device. A 90° signal generator 28 is electrically connected to the mixer 25, with signal generator 20 electrically connected to mixer 24. Signal generators 20 and 28 drive dielectrophoretic device electrodes 12' and 13'. Collected particles cause a change in the device impedance, as described above, and the output of the current sensor 21. Amplifiers 22 and 23 and mixers 24 and 25 measure the in-phase 26 and out-of phase 27 components of the devices complex impedances.

It has thus been shown that the present invention utilizes impedance measurements to detect the end-point for PCR DNA amplification. The invention provides an electronic detection approach that is less expensive then the presently utilized optical detection systems. While not shown, the fluidic device can be modified to incorporate reference electrodes located in insulated spaced relationship to electrodes 12 and 13, and the impedance sensor modified to utilize the reference signal. The impedance sensor of this invention can be used in counter biological warfare detectors to detect the presence of pathogens using PCR real-time detection methods, as well as in commercial assay systems such as clinical PCR that is currently using the Taqman assay.

While a particular embodiment of the apparatus of the present invention has been described and illustrated to exemplify and teach the principles of the invention, such is not intended to be limiting. Modifications and changes may become apparent to those skilled in the art, and it is intended that the invention be limited only by the scope of the appended claims.

What is claimed is:

1. A method for detecting the end-point for PCR DNA amplification comprising:
    providing at least a pair of electrodes in a fluidic channel,
    producing an electric field across the electrodes,
    directing a fluid containing single stranded DNA segments through the fluidic channel,
    directing at least one ionically labeled probe through the fluidic channel for attachment to a complementary DNA segment causing the release of a labeled ion,
    trapping the labeled ion in the electric field causing a conductivity change in the fluid between the electrodes,
    measuring the change in conductivity as a changing in the impedance between the pair of electrodes, and
    using the impedance measurement to detect the presence of the trapped labeled ion.

2. The method of claim 1, additionally including forming the electric field by supplying an AC or DC voltage across the pair of electrodes.

3. The method of claim 1, additionally including denaturing double stranded DNA into two single stranded DNA segments.

4. The method of claim 1, wherein the labeled ion is released by polymerase enzyme reaction.

5. The method of claim 1, additionally including providing an impedance sensor for measuring the conductivity change and detecting the presence of trapped labeled ions.

6. In a method for detecting the end-point for PCR DNA amplification, the improvement comprising,
    providing electrodes forming an electric field in a fluidic channel,
    utilizing an ionically labeled probe for attachment to a complementary DNA segment flowing through the fluidic channel to cause release of an ionic label,
    trapping the ionic label in the electric field causing a change in conductivity adjacent the electric field, and
    measuring the conductivity change as a change in impedance between the electrodes,
    and detecting the ionic label from impedance measurements.

7. The improvement of claim 6, additionally including forming the electric field by directing an AC or DC voltage across the electrodes.

8. The improvement of claim 6, additionally including forming the electrodes in spaced relation on a surface of the fluidic channel.

9. The improvement of claim 6, additionally including providing an impedance sensor for measuring the change in conductance caused by the trapped ionic label.

* * * * *